United States Patent [19]
Willms et al.

[11] Patent Number: 6,147,248
[45] Date of Patent: *Nov. 14, 2000

[54] 4-JOD-2[N-(N-ALKYL-AMINOCARBONYL)-AMINOSULFONYL]-BENZOIC ACID METHYL ESTER AND DERIVATIVED THEREOF AND METHOD FOR THEIR PRODUCTION

[75] Inventors: Lothar Willms, Hofheim; Harald Knorr, Frankfurt, both of Germany

[73] Assignee: Hoechst Schering AgrEvo GmbH, Berlin, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 09/214,041
[22] PCT Filed: Jun. 18, 1997
[86] PCT No.: PCT/EP97/03170
§ 371 Date: Dec. 23, 1998
§ 102(e) Date: Dec. 23, 1998
[87] PCT Pub. No.: WO98/00396
PCT Pub. Date: Jan. 8, 1998

[30] Foreign Application Priority Data

Jun. 28, 1996 [DE] Germany .............. 196 25 831

[51] Int. Cl.⁷ .................. C07C 303/40; C07C 311/18
[52] U.S. Cl. ........................................ 560/12; 560/13
[58] Field of Search ........................ 560/12, 13

[56] References Cited

U.S. PATENT DOCUMENTS

| | | | |
|---|---|---|---|
| 4,383,113 | 5/1983 | Levitt ................. | 544/211 |
| 4,566,898 | 1/1986 | Reap ................... | 71/93 |
| 5,463,081 | 10/1995 | Ort et al. ............. | 549/13 |

FOREIGN PATENT DOCUMENTS

WO 92/13845  8/1992  WIPO .

OTHER PUBLICATIONS

The Journal of the American Chemical Society, vol. 55, (1933), pp. 1649–1654.

*Primary Examiner*—Peter O'Sullivan
*Attorney, Agent, or Firm*—Frommer Lawrence & Haug LLP

[57] ABSTRACT

The invention relates to compounds of the formula (I)

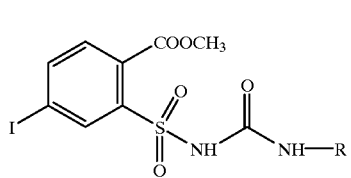

(I)

in which R=(subst.) alkyl or (subst.) cycloalkyl, which are suitable as intermediates for preparing herbicidal sulfonylureas. According to the invention, the compounds (I) are prepared by (a) diazotizing a compound of the formula (II)

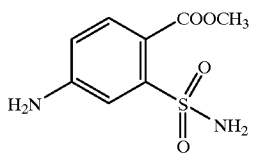

(II)

in the presence of an acid $H^+X^-$, where $X^-$ is an equivalent of an anion, to give the novel compounds (diazonium salts) of the formula (III)

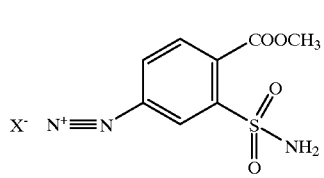

(III)

(b) reacting the compound of the formula (III) in the presence of iodide ions to give the compound (IV) and

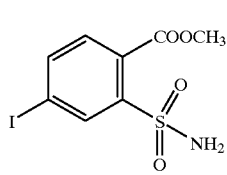

(IV)

(c) reacting the compound of the formula (IV) with an isocyanate of the formula (V)

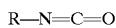

R—N=C=O    (V)

in which R is as defined in formula (I), to give the compound of the formula (I).

15 Claims, No Drawings

4-JOD-2[N-(N-ALKYL-AMINOCARBONYL)-AMINOSULFONYL]-BENZOIC ACID METHYL ESTER AND DERIVATIVED THEREOF AND METHOD FOR THEIR PRODUCTION

The invention relates to the technical field of the intermediates for the preparation of active compounds, in particular of herbicidal sulfonylureas.

It is known that ureas of the formula aryl-$SO_2$—NH—CO—NH—R, where aryl is an aryl radical with or without substitution and R is an alkyl radical, can in principle be reacted with phosgene to give the corresponding isocyanates of the formula aryl-$SO_2$—NCO which in turn can be employed for preparing herbicidally active sulfonylureas (EP-A-0584043; U.S. Pat. No. 4,566,898). To be able to apply the general method to the preparation of sulfonylureas of the series aryl=2-carbomethoxy-5-iodophen-1-yl, which are useful herbicidal sulfonylureas (WO-A-92/13845), it was the object to provide compounds of the formula (I)

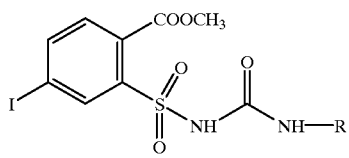

in which R is alkyl or cycloalkyl, each of the last two radicals being unsubstituted or substituted. Preferably, the object was to provide an effective process for preparing compounds of the formula (I).

Surprisingly, it is possible, as discussed in more detail below, to obtain the compounds of the formula (I) starting from compounds of the formula (II) via the intermediates (III) and (IV) in very good yields. The invention thus permits an effective preparation of herbicidal sulfonylureas and other active compounds.

The invention relates to a process for preparing N-substituted methyl 4-iodo-2-[N-(aminocarbonyl) aminosulfonyl]benzoates of the formula (I)

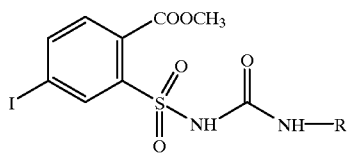

in which R is alkyl or cycloalkyl, each of the last two radicals being unsubstituted or substituted, and
preferably R is ($C_1$–$C_{12}$)alkyl which is unsubstituted or substituted by one or more radicals selected from the group consisting of halogen, ($C_1$–$C_6$)alkoxy, ($C_1$–$C_6$)alkylthio, ($C_1$–$C_6$)haloalkoxy and phenyl with or without substitution, or is ($C_3$–$C_{12}$)cycloalkyl which is unsubstituted or substituted by one or more radicals selected from the group consisting of halogen, ($C_1$–$C_4$)alkyl, ($C_1$–$C_4$)haloalkyl, ($C_1$–$C_4$)alkoxy, ($C_1$–$C_4$)haloalkoxy and ($C_1$–$C_6$)alkylthio, which comprises (a) diazotizing a compound of the formula (II)

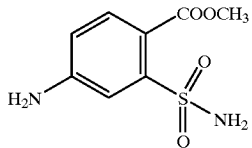

in the presence of an acid $H^+X^-$ where $X^{31}$ is an equivalent of an anion, for example $X^-$=$Cl^-$, $I^-$ or $HSO_4^-$, to give a compound (diazonium salt) of the formula (III)

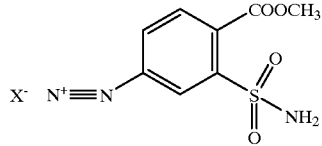

in which $X^-$ has the same meaning as in the acid $H^+X^-$, and (b) reacting the compound of the formula (III), after its isolation or, preferably, without isolation, in the presence of iodide ions to give a compound of the formula (IV)

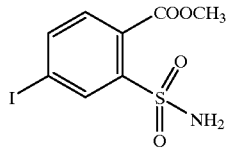

and c) reacting the compound of the formula (IV) with an isocyanate of the formula (V)

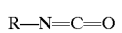

in which R is as defined in formula (I), to give the compound of the formula (I).

The invention furthermore provides individual steps of the process.

In the formula (I) and in the formulae used hereinbelow, the radicals alkyl, alkoxy, haloalkyl, haloalkoxy and alkylthio and the corresponding substituted radicals may in each case be straight-chain or branched in the carbon skeleton. Unless specifically mentioned, the lower carbon skeletons, for example those having 1 to 4 carbon atoms, are preferred for these radicals. Alkyl radicals, also in the composite meanings such as alkoxy, haloalkyl, etc., are, for example, methyl, ethyl, n- or i-propyl, n-, i-, t- or 2-butyl, pentyls, hexyls such as n-hexyl, i-hexyl and 1,3-dimethylbutyl, heptyls such as n-heptyls, 1-methylhexyl and 1,4-dimethylpentyl. Cycloalkyl is a carbocyclic saturated ring system, for example having 3 to 8 ring atoms, such as cyclopropyl, cyclobutyl, cyclopentyl, cyclohexyl and the like.

Halogen is, for example, fluorine, chlorine, bromine or iodine. Haloalkyl, -alkenyl and -alkynyl are alkyl, alkenyl and alkynyl, respectively, which are partially or fully substituted by halogen, preferably by fluorine, chlorine and/or bromine, in particular by fluorine or chlorine, for example $CF_3$, $CHF_2$, $CH_2F$, $CF_3CF_2$, $CH_2FCHCl_2$, $CCl_3$, $CHCl_2$, $CH_2CH_2Cl$; haloalkoxy is, for example, $OCF_3$, $OCHF_2$, $OCH_2F$, $CF_3CF_2O$, $OCH_2CF_3$ and $OCH_2CH_2Cl$; this applies correspondingly to haloalkenyl and other radicals substituted by halogen.

If substitutions are defined by "one or more radicals selected from a group of radicals", this applies both to the substitution by one or more identical radicals and to mono- or polysubstitution by different radicals. Phenyl with or without substitution is preferably phenyl which is unsubstituted or mono- or polysubstituted by identical or different radicals selected from the group consisting of halogen, alkyl, haloalkyl, alkoxy, haloalkoxy, alkylthio, hydroxyl, amino, nitro, cyano, azido, alkoxycarbonyl, alkylcarbonyl, formyl, carbamoyl, mono- and dialkylaminocarbonyl, substituted amino such as acylamino, mono- or dialkylamino, and alkylsulfinyl, haloalkylsulfinyl, alkylsulfonyl, haloalkylsulfonyl, preferably up to trisubstituted by identical or different radicals selected from the group consisting of halogen, $(C_1-C_4)$alkyl, $(C_1-C_4)$alkoxy, $(C_1-C_4)$haloalkyl, $(C_1-C_4)$haloalkoxy, CN and nitro, for example o-, m- and p-tolyl, dimethylphenyls, 2-, 3- and 4-chlorophenyl, 2-, 3- and 4-trifluoro- and -trichlorophenyl, 2,4-, 3,5-, 2,5- and 2,3-dichlorophenyl, o-, m- and p-methoxyphenyl.

The invention also relates to all stereoisomers embraced by the formula (I) and to mixtures of these. Such compounds of the formula (I) contain one or more asymmetric carbon atoms which are not specifically indicated in the formula (I). The stereoisomers which are possible and which are defined by their specific spatial form, such as enantiomers and diastereomers, are all embraced by the formula (I) and can be obtained from the stereoisomer mixtures by customary methods, or else be prepared by stereoselective reactions in combination with the use of stereochemically pure starting materials. The formula (I) also embraces tautomers of the compounds mentioned, in so far as they are generated by proton migration and in so far as they are chemically stable.

The compounds of the formula (I) can form salts where the hydrogen of the —$SO_2$—NH group, or else other acidic hydrogen atoms, is replaced by an agriculturally suitable cation. These salts are, for example, metal salts; preferably alkali metal or alkaline earth metal salts, in particular sodium and potassium salts, or else ammonium salts or salts with organic amines. Equally, salt formation can be effected by subjecting an acid to an addition reaction with basic groups such as, for example, amino and alkylamino. Acids which are suitable for this purpose are strong inorganic and organic acids, for example HCl, HBr, $H_2SO_4$ or $HNO_3$.

The compound of the formula (II) is known (cf. EP-A-382436, EP-A-382437) or can be prepared by standard methods from simple, commercially available compounds (cf. for example the preparation of the analogous isopropyl ester in J. Org. Chem. 27 (1962) 2177 ff.).

The diazotization of the compound of the formula (II) by process step (a) can be carried out under conditions which are customary per se for diazotization reactions. For example, the diazotization of the compound of the formula (II) in the presence of the acid $H^+X^-$, where $X^-$ is preferably $Cl^-$, $I^-$ or $HSO_4^-$, is carried out in aqueous solution and, if appropriate, preferably by adding an organic solvent which is inert under the reaction conditions, and by using a nitrite. The diazotization is, for example, carried out using an alkali metal nitrite such as $NaNO_2$ (sodium nitrite) in amounts of 1.0–1.2 mol of nitrite, preferably 1.01–1.05 mol of nitrite, per mole of the compound of the formula (II).

Suitable acids for the diazotization are mineral acids or strong organic acids. Preference is given to hydrohalic acids such as hydrochloric acid or hydriodic acid, or sulfuric acid.

The acid $H^+X^-$ is employed as usual in excess, based on the stoichiometric amount; in the case of n-valent acids where n is greater than 1, such as sulfuric acid (n=2), the stoichiometric amount for a monovalent acid is to be divided by n to obtain the stoichiometric amount for the n-valent acid. A monobasic acid is, for example, employed in an amount of from 5 to 15 mol per mole of compound of the formula (II), preferably 8 to 12 mol of $H^+X^-$ per mole of compound of the formula (II).

The solvent for the diazotization is water or a mixture of water and an organic solvent which is inert under the reaction conditions, for example selected from the group consisting of aromatic hydrocarbons with or without substitution such as toluene, chlorobenzene, dichlorobenzenes, chlorotoluenes or xylenes, halogenated aliphatic hydrocarbons such as dichloromethane and ethers such as diethyl ether, dioxane and tetrahydrofuran.

The temperature which is suitable for the diazotization to give the compound of the formula (III) can easily be determined in preliminary experiments; generally, the reaction is carried out in the temperature range from −5 to 50° C., preferably from 10 to 20° C., in particular from 15 to 20° C.

The diazonium salts of the compounds of the formula (III) can be isolated by customary methods, but attention has to be paid to the relatively low stability of the diazonium group; however, preference is given to employing the compounds (III) without intermediate isolation for preparing the compounds of the formula (IV).

The diazonium salts of the formula (III), preferably those where $X^-=I^-$ (iodide anion), are novel and likewise form part of the subject-matter of the invention.

The reaction of the compound (III) to give the compound of the formula (IV) by process step (b) is carried out in the same aqueous or aqueous-organic solvent or solvent mixture as in process step (a) or in a similar, modified solvent (mixture). In the reaction, the diazonium group is replaced by the iodine atom, and iodide ions are therefore required in the reaction mixture.

These iodide ions can, in the case where $X^-=I^-$, originate from the anion of the diazonium salt itself.

If $X^-$ differs from the iodide anion and is, for example, $Cl^-$, iodide has to be added in another form, for example as alkali metal iodide such as sodium iodide or potassium iodide. In this case, the amount is, for example, 1.1 to 1.5 mol of iodide per mole of the compound of the formula (III). Alternatively, the iodide can already have been added to the compound of the formula (II) at preliminary step (a).

The formation of the compound of the formula (IV) from the compound of the formula (III) usually occurs in the temperature range from 10 to 40° C., preferably from 15 to 30° C.

The preparation of the compound of the formula (IV) is carried out, for example, by initially charging the compound of the formula (II) in aqueous hydrochloric acid and admixing catalytic amounts of toluene, if appropriate together with a defoamer. At 15 to 20° C., an aqueous solution of $NaNO_2$ is slowly added, the mixture is stirred for some time and the excess of nitrite is destroyed using amidosulfonic acid. The resulting diazonium salt of the formula (III) (where $X^-=Cl^-$) is added as an aqueous solution at 15 to 20° C. to an aqueous solution of potassium iodide. The mixture is stirred for some time and the precipitate is then filtered off, washed with bisulfite (for example $NaHSO_3$) until free of iodide and dried.

Surprisingly, the preparation of the iodophenylsulfonamide (IV) via the diazonium salt (III) succeeds with very good yields. Yields of much more than 90% of theory can be obtained.

Taking known yields of similar reactions into consideration, such high yields were not to be expected. According to J. Am. Chem. Soc. 55 (1933) 1652, the diazotization of ethyl 4-aminobenzoate using sodium nitrite and hydrochloric acid and subsequent reaction with added potassium iodide gives ethyl 4-iodobenzoate in a yield of only 68.5% of theory; in comparison to this, the reaction proceeds surprisingly well with compounds of the formula (III), which, owing to the sulfonamido group, have an additional functional group.

The iodophenyl compound of the formula (IV) itself could hitherto only be prepared in insufficient yield. Thus, starting from methyl 4-iodo-2-chlorosulfonylbenzoate in the presence of ammonia, the compound of the formula (IV) is obtained in only about 75% yield (see WO 92/13845, Ex. 6, page 26); with this type of reaction, yield losses owing to ring closure to the saccharin derivative have been observed frequently. However, using the process according to the invention, the compound of the formula (IV) is obtained in very high yields and without the undesirable iodosaccharin.

In process step (c), the compound of the formula (IV) is reacted with an isocyanate of the formula R—N=C=O (V) to give a compound of the formula (I). The reaction is preferably carried out with base catalysis and in an inert solvent, the added organic solvents that have been mentioned for the process steps (a) and (b) also being suitable here; other organic solvents can also be employed, and suitable solvents can be found easily by comparison in preliminary experiments.

Preferred solvents for process step (c) are non-aqueous organic solvents which are inert under the reaction conditions, for example selected from the group consisting of aromatic hydrocarbons with or without substitution such as toluene, chlorobenzene, dichlorobenzenes, chlorotoluenes or xylenes, halogenated aliphatic hydrocarbons such as dichloromethane, ethers such as diethyl ether, dioxane and tetrahydrofuran and ketones such as acetone.

Preference is given to chlorobenzene.

Suitable bases are inorganic or organic bases, for example carbonates such as $K_2CO_3$, $Na_2CO_3$, substituted amines such as triethylamine, DBU (1,8-diazabicyclo[5.4.0]undec-7-ene) and the like; preference is given to a base such as $K_2CO_3$. The bases are employed for example in amounts of from 1 mol to 1.1 mol, preferably from 1.01 to 1.05 mol per mole of compound of the formula (IV).

The amounts of isocyanate of the formula (V) are, for example, 1.0–2.0 mol, preferably 1.01–1.1 mol, per mole of compound of the formula (IV). Preferred isocyanates used are methyl isocyanate, ethyl isocyanate, n-propyl isocyanate, isopropyl isocyanate, n-butyl isocyanate, i-, sec- or t-butyl isocyanate, n-pentyl isocyanate, n-hexyl isocyanate, cyclohexyl isocyanate, dodecyl isocyanate, preferably isocyanates where R is $(C_4$–$C_6)$alkyl.

When solvents such as toluene, xylene or chlorobenzene are used, the reaction temperature in process step (c) for preparing compounds of the formula (I) is preferably set in two stages. Initially, for example, the temperature is kept at 55–60° C. for 2 hours, and then at 90° C. for 5 to 10 hours, preferably for 6 to 9 hours. In the presence of solvents such as acetone, for example, the reaction is initially carried out with stirring at room temperature and then with stirring and under reflux for 4 to 10 hours, preferably 5 to 8 hours.

The preparation of the compound of the formula (I) is for example carried out by admixing the sulfonamide of the formula (IV) with $K_2CO_3$ and the isocyanate of the formula (V) in chlorobenzene and initially carrying out the reaction at 55 to 60° C. and then at 90° C. After cooling to room temperature, the reaction mixture is admixed with water and adjusted to pH 1–2 using 2n hydrochloric acid. The organic phase is separated off, washed free of acid and concentrated. The residue comprises the compounds of the formula (I) in high yields and very good purities.

Hitherto, the compounds of the formula (I) have been obtainable only in insufficient yields. Thus, for example, the desired butylsulfonylurea isopropyl 2-[N-(N-butylaminocarbonyl)aminosulfonyl]-4-chlorobenzoate is obtained by the reaction of isopropyl 2-(aminosulfonyl)-4-chlorobenzoate with butyl isocyanate in 2-butanone in a yield of only 44% of theory (U.S. Pat. No. 4,566,898, Ex. 5).

However, the compounds of the formula (I) are surprisingly obtained in very high yields in the process according to the invention. Using this method, only little waste is produced and volume yields are high. Thus, for the above-mentioned reasons, it was unforeseeable that the compounds of the formula (I) could be obtained, starting from the compound of the formula (IV) or the compound of the formula (II), in such a high yield or total yield over several steps.

In the following examples, quantities refer to weight, unless specifically defined otherwise.

EXAMPLE 1

Methyl 4-iodo-2-aminosulfonylbenzoate (IV)

1000 g (4.34 mol) of methyl 4-amino-2-aminosulfonylbenzoate and 3400 ml of $H_2O$ are admixed rapidly with 3700 ml of concentrated hydrochloric acid (37% strength). 10 ml of toluene are added to this mixture. The mixture is cooled to 15° C. and a solution of 315 g of $NaNO_2$ (4.56 mol) in 1740 ml of $H_2O$ is added within a period of 1 h (h=hour) at 15–20° C. Stirring is continued for 1 h and the excess of nitrite is destroyed using amidosulfonic acid. In a second vessel, 1082 g of potassium iodide (6.51 mol) and 7000 ml of $H_2O$ are initially charged. At 15 to 20° C., the diazonium salt solution is added over a period of 1 to 2 h. The resulting suspension is diluted with 10 liters of $H_2O$ and the precipitate is filtered off with suction. The filter cake is then washed free of iodine using a mixture of 435 g of $Na_2S_2O_5$ in 8.5 liters of $H_2O$, and then washed neutral with 25 liters of $H_2O$. The compound of the formula (IV) is obtained in a quantity of 1771 g (moist). After drying at 50° C. in vacuo (=under reduced pressure), 1403 g (94.8% of theory) of methyl 4-iodo-2- aminosulfonylbenzoate (sulfonamide of the formula IV) of a melting point of 175–177° C. are obtained.

EXAMPLE 2

Methyl 4-iodo-2-[N-(N-butylaminocarbonyl) aminosulfonyl]benzoate (I)

34.1 g (0.1 mol) of the sulfonamide of the formula (IV) from Example 1 and 14.7 g of $K_2CO_3$ (0.105 mol) are admixed with 10.6 g of n-butyl isocyanate (98% pure) (0.105 mol) in 250 ml of chlorobenzene, and the mixture is kept at 55 to 60° C. for 2 hours. The mixture is then stirred at 90° C. for 8.5 h. The mixture is cooled to room temperature and initially 200 ml of water and then 2n of hydrochloric acid are added until the pH has reached 1–2. The organic phase is separated off and washed free of acid using four times 50 ml of water. The solvent is removed under reduced pressure, and 43.8 g of the desired compound of the formula (I) (99.3% of theory) of melting point 128 to 130° C. remain.

COMPARATIVE EXAMPLE (U.S. Pat. No. 4,566,898)

A mixture of 1063.4 g of isopropyl 2-(aminosulfonyl)-4-chlorobenzoate, 590.4 g of n-butyl isocyanate and 590.4 g of K₂CO₃ in 10.8 liters of 2-butanone are heated under reflux overnight. After cooling to room temperature, the reaction mixture is in each case poured into 10 liters of ice-water. The aqueous phase is extracted with 9 liters of methylene chloride. The aqueous phase is acidified to pH 1.0 using concentrated HCl, and the resulting precipitate is filtered off. After drying, 714.6 g of isopropyl 2-[N-(N-butylaminocarbonyl)aminosulfonyl]-4-chlorobenzoate (44% of theory) of melting point 129–132° C. are obtained.

What is claimed:

1. A compound of the formula (I),

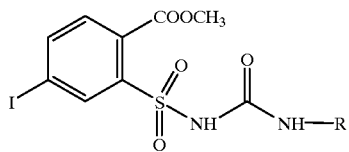

(I)

in which
R is alkyl or cycloalkyl, each of the last two radicals being unsubstituted or substituted.

2. A compound as claimed in claim 1, wherein
R is (C₁–C₁₂)alkyl which is unsubstituted or substituted by one or more radicals selected from the group consisting of halogen, (C₁–C₆)alkoxy, (C₁–C₆)alkylthio, (C₁–C₆)haloalkoxy and phenyl with or without substitution, or is (C₃–C₁₂)cycloalkyl which is unsubstituted or substituted by one or more radicals selected from the group consisting of halogen, (C₁–C₄)alkyl, (C₁–C₄)haloalkyl, (C₁–C₄)alkoxy, (C₁–C₄)haloalkoxy and (C₁–C₆)alkylthio.

3. A compound as claimed in claim 1, wherein
R is (C₁–C₁₂)alkyl which is unsubstituted or substituted by one or more radicals selected from the group consisting of halogen, (C₁–C₄)alkoxy and phenyl, or is (C₃–C₁₂)cycloalkyl.

4. A compound as claimed in claim 1, wherein
R is n-butyl.

5. A process for preparing compounds of the formula

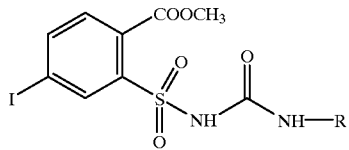

(I)

in which
R is alkyl or cycloalkyl, each of the last two radicals being unsubstituted or substituted
which comprises (a) diazotizing a compound of the formula

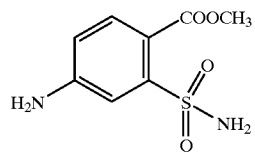

(II)

in the presence of an acid H⁺X⁻, where X⁻ is an equivalent of a anion, to produce a diazonium salt of the formula

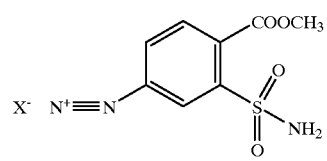

(III)

in which X⁻ has the same meaning as in the acid H⁺X⁻, (b) reacting a compound of formula (III) with iodide ions to give a compound of the formula

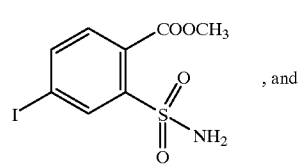

(IV)

, and (c) reacting a compound of formula (IV) with an isocyanate of the formula

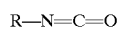

R—N=C=O in which R is defined above, to give a compound of formula I.

6. The process according to claim 5 wherein the acid in step (a) is hydrohalic acid.

7. The process according to claim 5, wherein X⁻ is I⁻.

8. The process according to claim 5, wherein the compound of formula (IV) is reacted with an isocyanate of formula (V) in the presence of a base and an inert solvent.

9. The process according to claim 5, wherein the base is K₂CO₃, NaCO₃, triethylamine, and DBU; the insert solvent is toluene, chlorobenzene, dichlorobenzene, chlorotoluenes, xylenes, dichloromethane, diethyl ether, dioxane, tetrahydrofuran or acetone; and the isocyanate is ethyl isocyanate, n-propyl isocyanate, n-butyl isocyanate, i-, sec- or t-butyl isocyanate, n-pentyl isocyanate, n-hexyl isocyanate, cyclohexyl isocyanate and dodecyl isocyanate.

10. The process according to claim 9 wherein 1 mol to 1.1 mole of base per mol of compound of formula (IV) and 1.0 to 2.0 mol of isocyanate per mol of compound of formula (IV) are used.

11. The process according to claim 9, wherein the step (c) is carried out in two stages at two different reaction temperatures, where temperature in the first stage is between 55 to 60° C. and the temperature in the second stage is 90° C.

12. A process for preparing a compound of the formula (I)

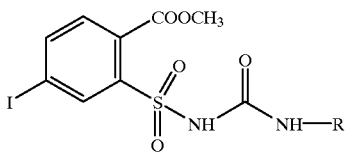

in which
R is alkyl or cycloalkyl, each of the last two radicals being unsubstituted or substituted,
which comprises reacting a compound of the formula (IV)

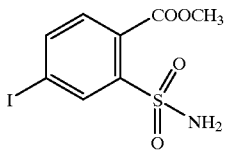

with an isocyanate of the formula (V)

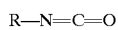 (V)

in which R is as defined in formula (I),
optionally in the presence of a base and an inert solvent.

13. The process according to claim 12, wherein the base is $K_2CO_3$, $NaCO_3$, triethylamine, and DBU; the insert solvent is toluene, chlorobenzene, dichlorobenzene, chlorotoluenes, xylenes, dichloromethane, diethyl ether, dioxane, tetrahydrofuran or acetone; and the isocyanate is ethyl isocyanate, n-propyl isocyanate, n-butyl isocyanate, i-, sec- or t-butyl isocyanate, n-pentyl isocyanate, n-hexyl isocyanate, cyclohexyl isocyanate and dodecyl isocyanate.

14. The process according to claim 12, wherein 1 mol to 1.1 mole of base per mol of compound of formula (IV) and 1.0 to 2.0 mol of isocyanate per mol of compound of formula (IV) are used.

15. The process according to claim 12 wherein the reaction is carried out in at two different stages at two different reaction temperatures, where temperature in the first stage is between 55 to 60° C. and the temperature in the second stage is 90° C., the solvent is chlorobenzene or acetone and the base is $K_2CO_3$.

* * * * *